(12) United States Patent
Song et al.

(10) Patent No.: US 9,987,039 B2
(45) Date of Patent: Jun. 5, 2018

(54) MEDICAL INTERVENTION APPARATUS

(71) Applicants: Ho Seok Song, Gwangmyeong-si (KR); Min Kyo Cho, Seongnam-si (KR); Jun Woo Park, Yongin-si (KR); Hong Ho Kim, Seoul (KR)

(72) Inventors: Ho Seok Song, Gwangmyeong-si (KR); Min Kyo Cho, Seongnam-si (KR); Jun Woo Park, Yongin-si (KR); Hong Ho Kim, Seoul (KR)

(73) Assignee: Curexo, Inc., Seoul (KR)

( * ) Notice: Subject to any disclaimer, the term of this patent is extended or adjusted under 35 U.S.C. 154(b) by 431 days.

(21) Appl. No.: 14/723,036

(22) Filed: May 27, 2015

(65) Prior Publication Data
US 2015/0374406 A1 Dec. 31, 2015

(30) Foreign Application Priority Data

Jun. 27, 2014 (KR) .................. 10-2014-0080142

(51) Int. Cl.
*A61B 17/34* (2006.01)
*A61B 46/10* (2016.01)
*A61B 90/11* (2016.01)
*A61M 5/158* (2006.01)
*A61B 90/00* (2016.01)

(52) U.S. Cl.
CPC .......... *A61B 17/3403* (2013.01); *A61B 46/10* (2016.02); *A61B 90/11* (2016.02); *A61M 5/158* (2013.01); *A61B 2017/3405* (2013.01); *A61B 2017/3409* (2013.01); *A61B 2090/0813* (2016.02); *A61M 2005/1585* (2013.01); *A61M 2205/02* (2013.01)

(58) Field of Classification Search
CPC ..... A61B 17/3403; A61B 46/10; A61B 90/11; A61B 2090/0813; A61B 2017/3405; A61B 2017/3409; A61M 5/158; A61M 2205/02; A61M 2005/1585
See application file for complete search history.

(56) References Cited

U.S. PATENT DOCUMENTS

| 3,835,854 | A | * | 9/1974 | Jewett | A61M 25/0113 604/159 |
| 4,383,532 | A | * | 5/1983 | Dickhudt | A61M 25/0113 607/117 |
| 7,175,635 | B2 | * | 2/2007 | Loser | A61B 17/3403 606/130 |
| 8,657,761 | B2 | | 2/2014 | Kim et al. | |

* cited by examiner

*Primary Examiner* — Lauren P Farrar
(74) *Attorney, Agent, or Firm* — Andrew D. Fortney; Central California IP Group, P.C.

(57) ABSTRACT

Disclosed is a medical intervention apparatus. The medical intervention apparatus includes a needle rotation unit configured to include a first needle rotation member, a second needle rotation member that is disposed to be separated from the first needle rotation member, and a first driver that drives the first and second needle rotation members to rectilinearly move in opposite directions and a needle insertion unit configured to insert a needle, which is inserted between the first needle rotation member and the second needle rotation member, into a target.

20 Claims, 8 Drawing Sheets

MEDICAL INTERVENTION APPARATUS

CROSS-REFERENCE TO RELATED APPLICATIONS

This application claims the benefit of the Korean Patent Application No. 10-2014-0080142 filed on Jun. 27, 2014, which is hereby incorporated by reference as if fully set forth herein.

BACKGROUND

Field of the Invention

The present invention relates to a medical intervention apparatus, and more particularly, to a medical intervention apparatus that protects medical staffs from radiation exposure, decreases the number of times an operation of inserting a needle is performed, increases a needle supporting force, enables a plurality of needles having different thicknesses to be all used, secures a radiolucency of near an insertion point, and enhances a sterilizability of an apparatus.

Discussion of the Related Art

Generally, intervention is technology that inserts a medical instrument into a human body and performs an interventional procedure while observing the inside of the human body through an imaging apparatus. Intervention is medical technology which is used for a surgical procedure and internal medicine such as tissue biopsy, dilation, medicine injection, etc. Intervention which uses a needle as a medical instrument is called a needle intervention.

In the needle intervention, a needle is inserted into a human body, and an interventional procedure is performed. In the related art, a medical staff inserts a needle into a human body and performs an interventional procedure while looking at the inside of the human body by using a radiographic apparatus such as a fluoroscopic apparatus, a computed tomography (CT) apparatus, or the like. For this reason, intervention of the related art has the following problems.

First, in the related art needle intervention, a medical staff directly and manually inserts a needle into a human body. Therefore, the medical staff performs an interventional procedure in a state where the medical staff is directly exposed to a harmful environment caused by radiation which is generated from an imaging apparatus such as a radiographic apparatus or the like. For this reason, the related art of needle intervention cannot protect medical staffs from radiation exposure.

Second, since the related art of needle intervention is performed dependently on an experience, a sense, and/or the like of a medical staff, it is difficult to insert a needle into an accurate position. For example, in the related art, an interventional procedure is performed as follows.

First, an image of a treated part of a patient is captured in a room including an imaging apparatus before an interventional procedure, and then, the patient is moved to an operation room. Subsequently, in a case where an operator inserts a needle, an assistant such as a nurse or the like checks a needle insertion position and orientation with eyes at a position far away from the operator and the patient, and verbally provides the operator with information about whether the position and orientation of needle are accurate. Subsequently, the operator approximately adjusts the needle position and orientation dependently on an experience, a sense, and/or the like, based on approximate information provided from the assistant and temporarily inserts a portion of a needle into a body of the patient. Subsequently, the image of the treated part is re-captured for checking whether the needle is accurately inserted. Subsequently, the operator repeats the above-described process in order for the needle to be inserted into a desired position.

As described above, in the related art of needle intervention, since a needle inserting operation is repeatedly performed for inserting a needle into a desired position, patients suffer pain and agony, and a burden is applied to medical staffs. Also, in the related art of needle intervention, since a needle inserting operation is repeated a plurality of times for inserting a needle into an accurate position, a problem where patients and medical staffs are exposed to radiation increases more.

SUMMARY

Accordingly, the present invention is directed to provide a medical intervention apparatus that substantially obviates one or more problems due to limitations and disadvantages of the related art.

An aspect of the present invention is directed to provide a medical intervention apparatus that automatically performs a needle inserting operation, thereby protecting medical staffs from radiation exposure.

Another aspect of the present invention is directed to provide a medical intervention apparatus that decreases the number of times an operation of inserting a needle is performed, for inserting the needle into an accurate position and enhances an accuracy of a needle inserting operation.

Another aspect of the present invention is directed to provide a medical intervention apparatus that increases a needle supporting force and enables a plurality of needles having different thicknesses to be all used.

Another aspect of the present invention is directed to provide a medical intervention apparatus that secures a radiolucency of near an insertion point and enhances a sterilizability of a device.

Additional advantages and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these and other advantages and in accordance with the purpose of the invention, as embodied and broadly described herein, there is provided a medical intervention apparatus including: a needle rotation unit configured to include a first needle rotation member, a second needle rotation member that is disposed to be separated from the first needle rotation member, and a first driver that drives the first and second needle rotation members to rectilinearly move in opposite directions; and a needle insertion unit configured to insert a needle, which is inserted between the first needle rotation member and the second needle rotation member, into a target.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Reference will now be made in detail to the exemplary embodiments of the present invention, examples of which are illustrated in the accompanying drawings. Wherever possible, the same reference numbers will be used throughout the drawings to refer to the same or like parts.

In the specification, in adding reference numerals for elements in each drawing, it should be noted that like reference numerals already used to denote like elements in other drawings are used for elements wherever possible. The terms described in the specification should be understood as follows.

As used herein, the singular forms "a", "an" and "the" are intended to include the plural forms as well, unless the context clearly indicates otherwise. The terms "first" and "second" are for differentiating one element from the other element, and these elements should not be limited by these terms.

It should be further understood that the terms "comprises", "comprising,", "has", "having", "includes" and/or "including", when used herein, specify the presence of stated features, integers, steps, operations, elements, and/or components, but do not preclude the presence or addition of one or more other features, integers, steps, operations, elements, components, and/or groups thereof.

The term "at least one" should be understood as including any and all combinations of one or more of the associated listed items. For example, the meaning of "at least one of a first item, a second item, and a third item" denotes the combination of all items proposed from two or more of the first item, the second item, and the third item as well as the first item, the second item, or the third item.

Figure 1:
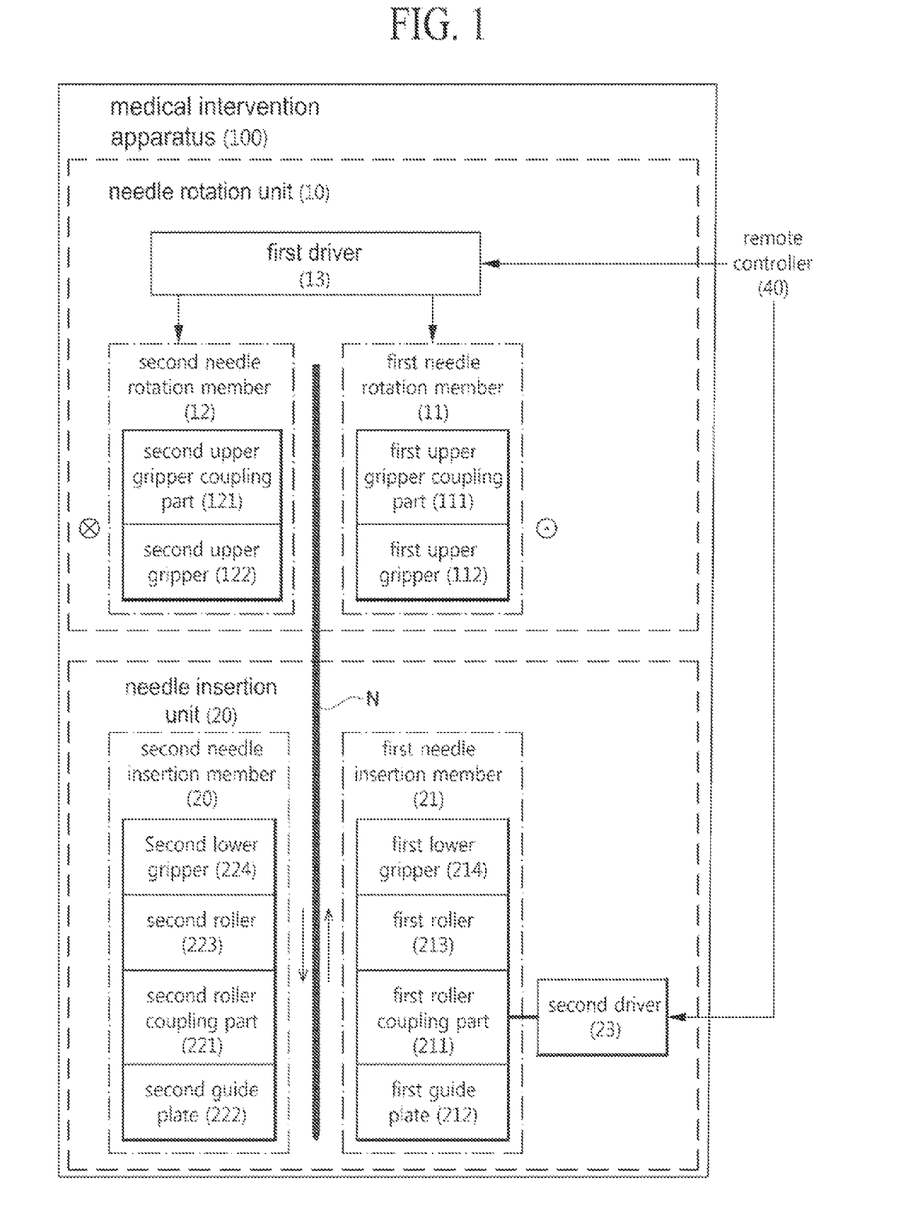
FIG. 1 is a whole block diagram of a medical intervention apparatus according to an embodiment of the present invention.

A medical intervention apparatus 100 according to an embodiment of the present invention may be coupled to, for example, an arm of a medical robot. The medical intervention apparatus 100 according to an embodiment of the present invention, as illustrated in FIG. 1, may include a needle rotation unit 10 and a needle insertion unit 20. The needle rotation unit 10 and the needle insertion unit 20 may be controlled by a remote controller 40. The needle rotation unit 10 and the needle insertion unit 20 may be partially made of a radiolucent material (for example, plastic), and thus, a radiolucency of near an insertion point is secured.

The needle rotation unit 10 may include a first needle rotation member 11, a second needle rotation member 12 that is disposed to be separated from the first needle rotation member 11, and a first driver 13 that drives the first and second needle rotation members 11 and 12.

The first needle rotation member 11 may move backward and forward with respect to a needle N according to a driving force transferred from the first driver 13. The first needle rotation member 11 may include a first upper gripper coupling part 111 and a first upper gripper 112. The first upper gripper 112 may be detachably attached to the first upper gripper coupling part 111.

The second needle rotation member 12 may move backward and forward with respect to the needle N according to the driving force transferred from the first driver 13. The second needle rotation member 12 may include a second upper gripper coupling part 121 and a second upper gripper 122. The second upper gripper 122 may be detachably attached to the second upper gripper coupling part 121.

The first driver 13 may include a motor, a timing belt which is disposed on a driving shaft of the motor and an idler pulley, an upper belt bracket which is disposed on the timing belt, and a lower belt bracket which is disposed under the timing belt. The upper belt bracket may be coupled to a module to which the first upper gripper coupling part 111 is fixed, and the lower belt bracket may be coupled to a module to which the second upper gripper coupling part 121 is fixed.

The first driver 13 may drive the first and second needle rotation members 11 and 12 to move backward and forward with respect to the needle N. Also, the first driver 13 may drive the first needle rotation member 11 to be closer to or farther away from the second needle rotation member 12.

The needle insertion unit 20 may insert the needle N, which is inserted between the first needle rotation member 11 and the second needle rotation member 12, into a target. The needle insertion unit 20, as illustrated in FIG. 1, may include a first needle insertion member 21, a second needle insertion member 22, and a second driver 23.

The first needle insertion member 21 may include a first roller coupling part 211 that rotates according to a driving force transferred from the second driver 23, a first guide plate 212 that is inserted into a roller bracket of the first roller coupling part 211 and includes a first guide groove that is provided to guide the needle N, a first roller 213 that is detachably attached to the first roller coupling part 211, and a first lower gripper 214 that is detachably attached to the first roller 213.

The second needle insertion member 22 may include a second roller coupling part 221, a second guide plate 222 that is inserted into a roller bracket of the second roller coupling part 221 and includes a second guide groove that is provided to guide the needle N, a second roller 223 that is detachably attached to the second roller coupling part 221, and a second lower gripper 224 that is detachably attached to the second roller 223.

The second driver 23 may drive the first roller coupling part 211 in order for the first roller 213 of the first needle insertion member 21 to rotate. When the first roller 213 rotates, the first lower gripper 214 may rotate, and thus, the first and second lower grippers 214 and 224 may rotate to move the needle N upward and downward. The second driver 23 may drive the first needle insertion member 21 to be closer to or farther away from the second needle insertion member 22.

Figure 2:
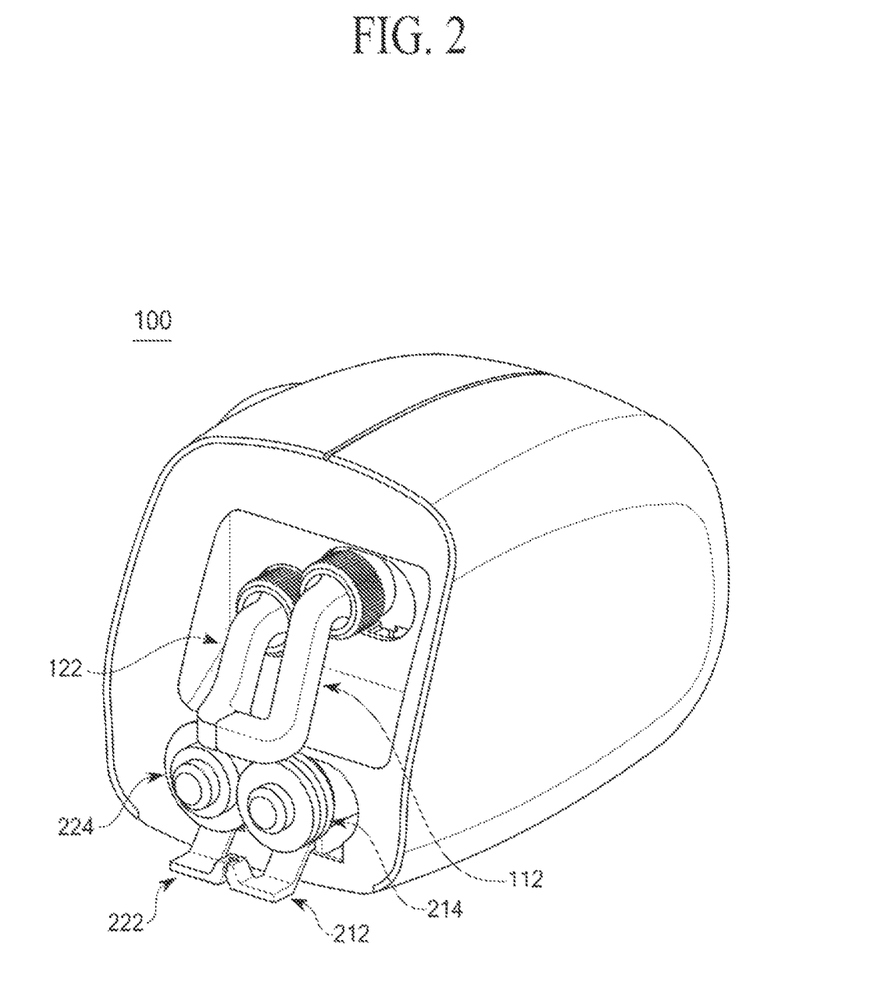
FIG. 2 is a schematic perspective view of an external appearance of the medical intervention apparatus according to an embodiment of the present invention.
Figure 3:
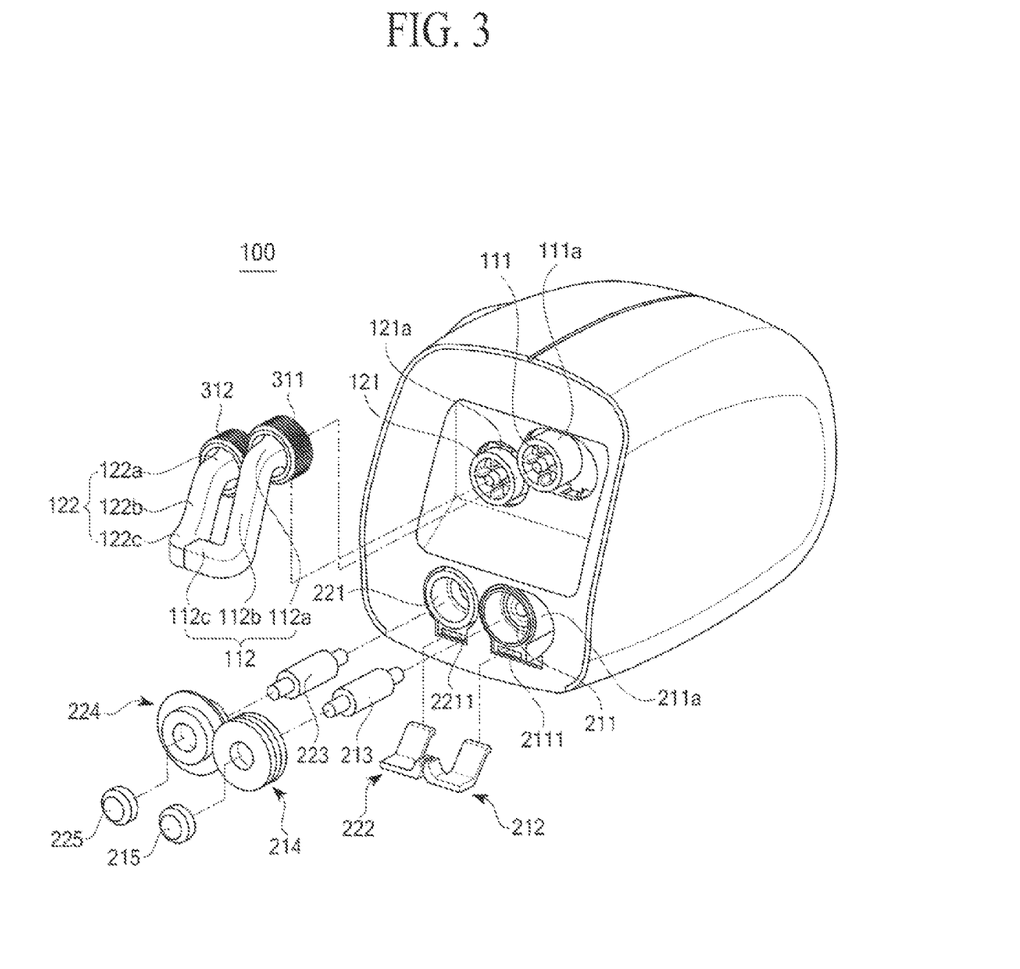
FIG. 3 is a partially exploded perspective view of the medical intervention apparatus illustrated in FIG. 2.

FIG. 2 is a schematic perspective view of an external appearance of the medical intervention apparatus 100 according to an embodiment of the present invention, and FIG. 3 is a partially exploded perspective view of the medical intervention apparatus 100 illustrated in FIG. 2. To describe the medical intervention apparatus 100 according to an embodiment of the present invention with reference to FIGS. 2 and 3, the first upper gripper 112 may be coupled to the first upper gripper coupling part 111, and the second upper gripper 122 may be coupled to the second upper gripper coupling part 121.

A first fastening member 311 may be fastened to a tap 111a of the first upper gripper coupling part 111, and the first fastening member 311 may support the first upper gripper 112 so that the first upper gripper 112 coupled to the first upper gripper coupling part 111 does not easily fall out. A second fastening member 312 may be fastened to a tap 121a of the second upper gripper coupling part 121, and the second fastening member 312 may support the second upper gripper 122 so that the second upper gripper 122 coupled to the second upper gripper coupling part 121 does not easily fall out. The first fastening member 311 may include a plurality of grooves that are arranged at certain intervals on an outer circumference surface thereof in order for a user to easily fasten the first upper gripper 112, and the second fastening member 312 may include a plurality of grooves that are arranged at certain intervals on an outer circumference surface thereof in order for the user to easily fasten the second upper gripper 122.

The first upper gripper 112 may include a connecting part 112a, a supporting part 112b, and a gripping part 112c that grips the needle N. The second upper gripper 122 may include a connecting part 122a, a supporting part 122b, and a gripping part 122c that grips the needle N. A whole shape of the first upper gripper 112 may be the same as that of the second upper gripper 122. However, the supporting part 112b of the first upper gripper 112 may be implemented longer than the supporting part 122b of the second upper gripper 122. The gripping part 112c of the first upper gripper 112 and the gripping part 122c of the second upper gripper 122 may be implemented to face each other.

Figure 5:
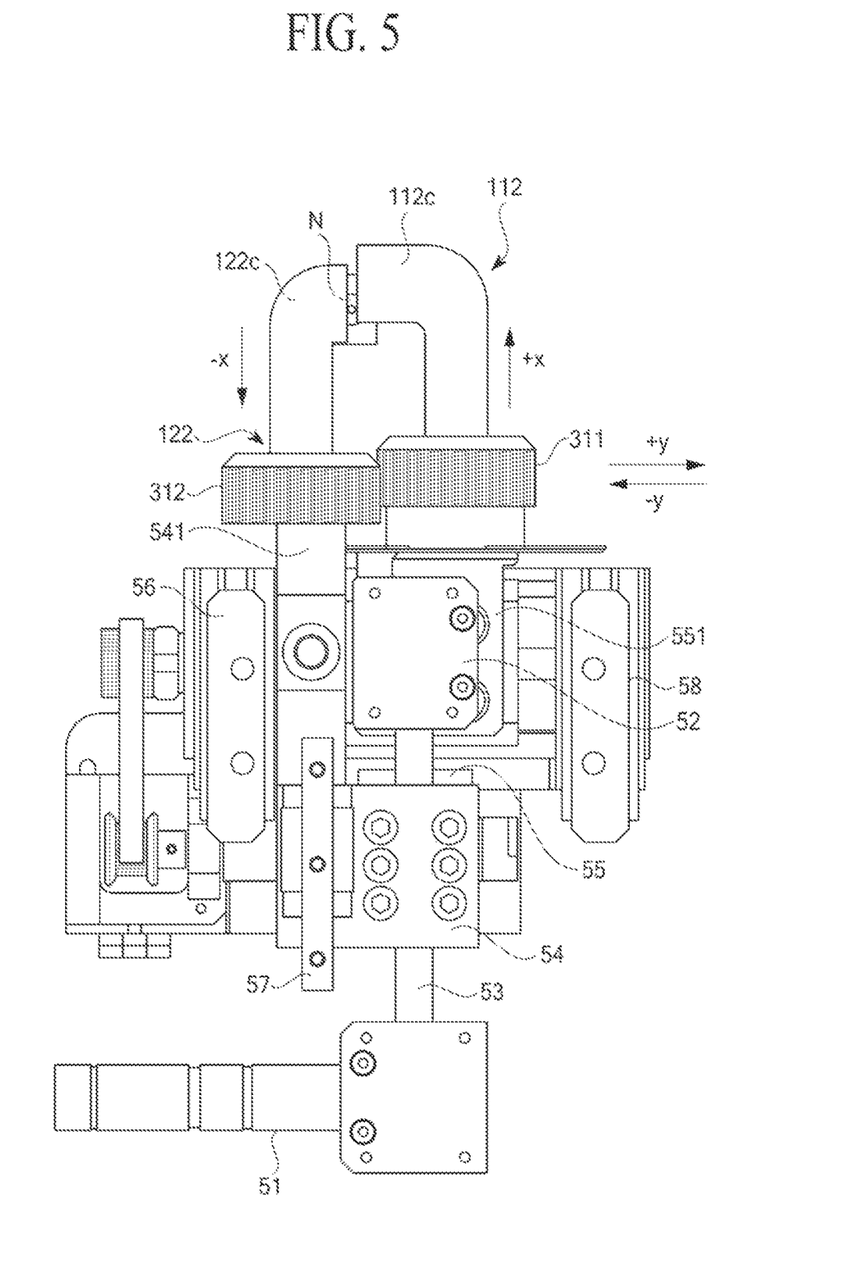
FIG. 5 is a bottom view when a user views an internal machine structure of the medical intervention apparatus according to an embodiment of the present invention in a direction from a bottom to a top.

Here, referring to FIG. 5, when the first upper gripper coupling part 111 moves in a +x direction and the second upper gripper coupling part 121 moves in a −x direction, the first upper gripper 112 may move in the +x direction, and the second upper gripper 122 may move in the −x direction, namely, the first and second upper grippers 122 and 122 may move in opposite directions. Therefore, the first and second upper grippers 112 and 122 may rotate the needle N gripped by the gripping parts 112c and 122c.

Figure 4A:
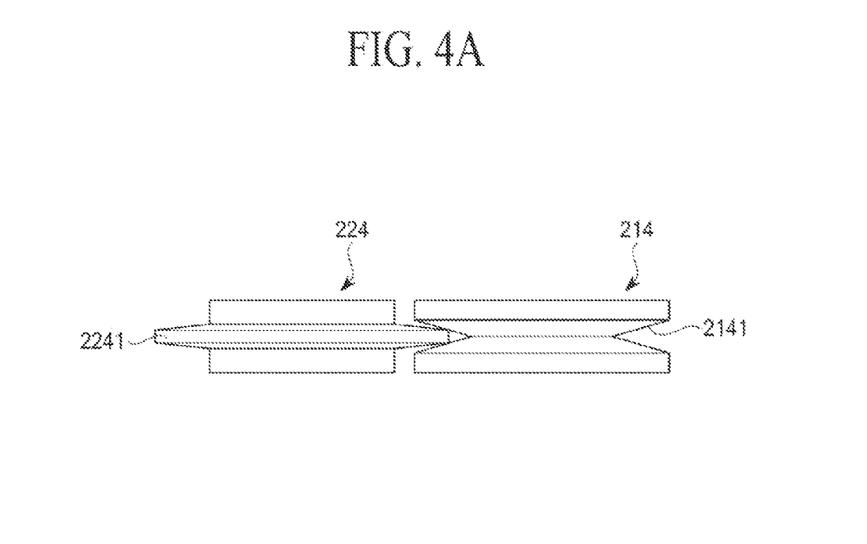
FIG. 4A is an exemplary diagram for describing first and second lower grippers according to an embodiment of the present invention.

The first guide plate 212 and the second guide plate 222 are as illustrated in FIG. 4A. Referring to FIG. 4A, the first guide plate 212 may include a first guide groove 212a, which guides the needle N, and an accommodating groove 212b that accommodates an end of the needle N and is connected to the first guide groove 212a. The second guide plate 222 may include a second guide groove 222a that guides the needle N.

Referring again to FIG. 3, the first roller 213 may be coupled to the first roller coupling part 211, and the second roller 223 may be coupled to the second roller coupling part 221. The first lower gripper 214 may be coupled to the first roller 213, and the second lower gripper 224 may be coupled to the second roller 223. The first guide plate 212 may be inserted into an insertion groove 2111 that is provided in the roller bracket 211a of the first roller coupling part 211. The second guide plate 222 may be inserted into an insertion groove 2211 that is provided in the roller bracket 221a of the second roller coupling part 221.

The first lower gripper 214 and the second lower gripper 224 are as illustrated in FIG. 4A. Referring to FIG. 4A, the first lower gripper 214 may include a needle contact groove 2141 that is provided along a circumference to have a shape where a width is progressively narrowed in a direction from an outer circumference surface to a center portion. The second lower gripper 224 may include a protrusion 2241 that is inserted into the needle contact groove 2141 of the first lower gripper 214. Three points of a needle may be supported by the needle contact groove 2141 of the first lower gripper 214 and the protrusion 2241 of the second lower gripper 224. The needle contact groove 2141 of the first lower gripper 214 and the protrusion 2241 of the second lower gripper 224 enable a plurality of needles having different thicknesses to be all used.

Each of the first upper gripper 112, the second upper gripper 122, the first lower gripper 214, the second lower gripper 224, the first guide plate 212, the second guide plate 222, the first roller 213, the second roller 223, the first fastening member 311, and the second fastening member 312 applied to the present invention may be a sterilized disposable element. Therefore, the medical intervention apparatus 100 according to an embodiment of the present invention may use a sterilization membrane that isolates an unsterilized part from a sterilized disposable element.

Figure 6:
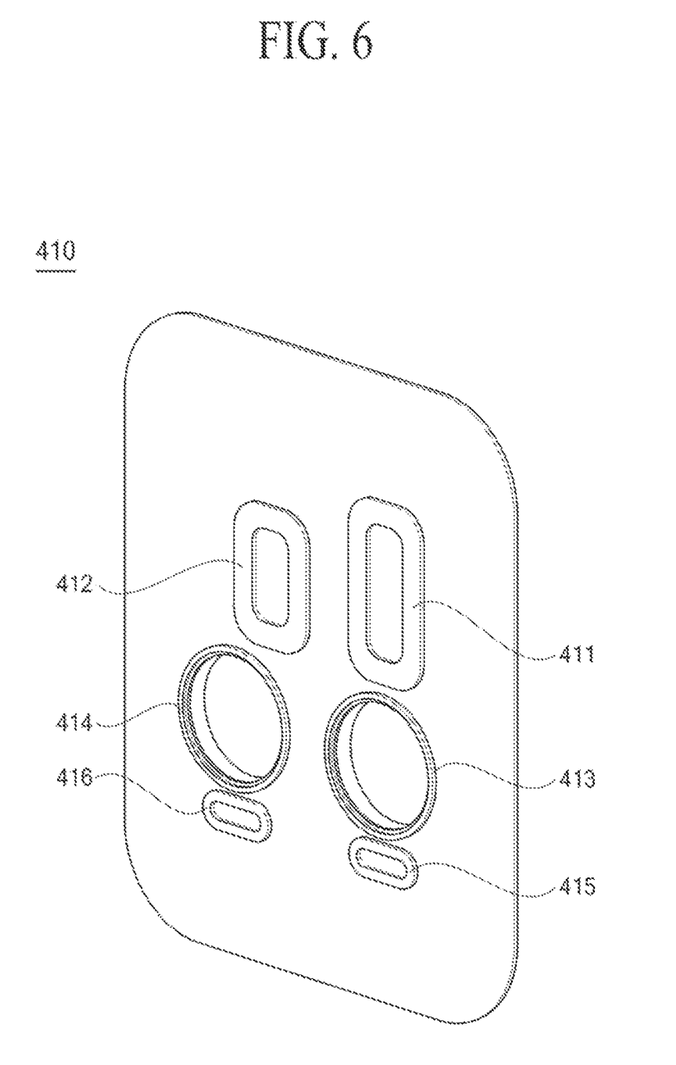
FIG. 6 is an exemplary diagram for describing a sterilization membrane according to an embodiment of the present invention.

A sterilization membrane 410 according to an embodiment of the present invention, as illustrated in FIG. 6, may include a first fitting part 411 that is fitted into the tap (111a in FIG. 3) of the first upper gripper coupling part 111, a second fitting part 412 that is fitted into the tap (121a in FIG. 3) of the second upper gripper coupling part 121, a third fitting part 413 that is fitted into the roller bracket (211a in FIG. 3) of the first roller coupling part 211, a fourth fitting part 414 that is fitted into the roller bracket (221a in FIG. 3) of the second roller coupling part 221, a fifth fitting part 415 into which the first guide plate (212 in FIG. 3) is fitted, and a sixth fitting part 416 into which the second guide plate (222 in FIG. 3) is fitted.

The sterilization membrane 410 according to an embodiment of the present invention may be formed of, for example, a material such as vinyl or the like. The first fitting part 411 and the second fitting part 412 may be each formed of an elastic material. In the third fitting part 413 and the fourth fitting part 414, a cap which is press-fitted and fixed to a corresponding roller bracket may be fixed to vinyl and molded. The sterilization membrane 410 according to an embodiment of the present invention may be fitted before a sterilized disposable element is assembled.

FIG. 5 is a bottom view when a user views a machine structure coupled to the inside of the medical intervention apparatus 100 according to an embodiment of the present invention in a direction from a bottom to a top. The machine structure illustrated in FIG. 5 may include a motor 51, a timing belt 53 that is disposed on a driving shaft of the motor 51 and an idler pulley mounted on an idler pulley bracket 52, a lower belt bracket 54 that is disposed under the timing belt 53, and an upper belt bracket 55 that is disposed on the timing belt 53.

In FIG. 5, the upper belt bracket 55 may be coupled to a module 551 to which the first upper gripper coupling part (111 in FIG. 3) is fixed, and the lower belt bracket 54 may be coupled to a module 541 to which the second upper gripper coupling part (121 in FIG. 3) is fixed. The machine structure illustrated in FIG. 5 may include first to third linear motion (LM) guides 56 to 58 that guide the module 551, to which the first upper gripper coupling part (111 in FIG. 3) is fixed, and the module 541, to which the second upper gripper coupling part (121 in FIG. 3) is fixed, to rectilinearly move. Particularly, the third LM guide 58 may guide the module 551, to which the first upper gripper coupling part (111 in FIG. 3) is fixed, to rectilinearly move in a ±y direction.

Figure 7A:
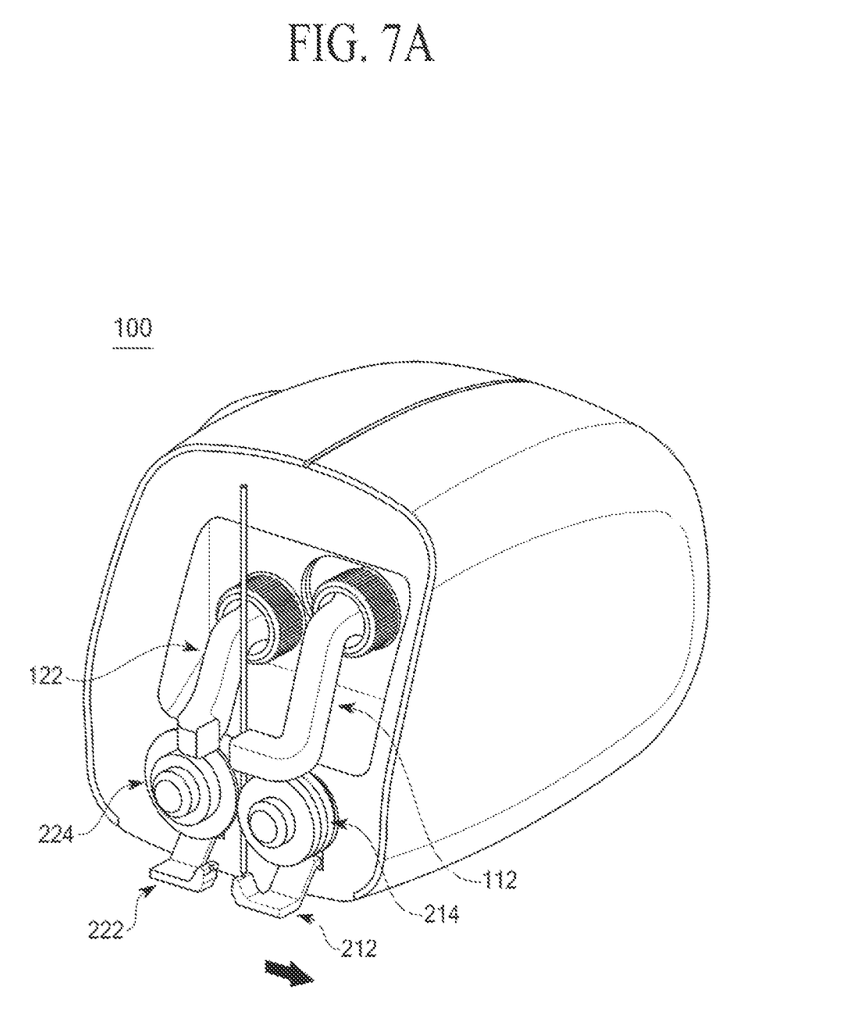
FIGS. 7A and 7B are exemplary diagrams for describing an operation of the medical intervention apparatus according to an embodiment of the present invention.
Figure 7B:
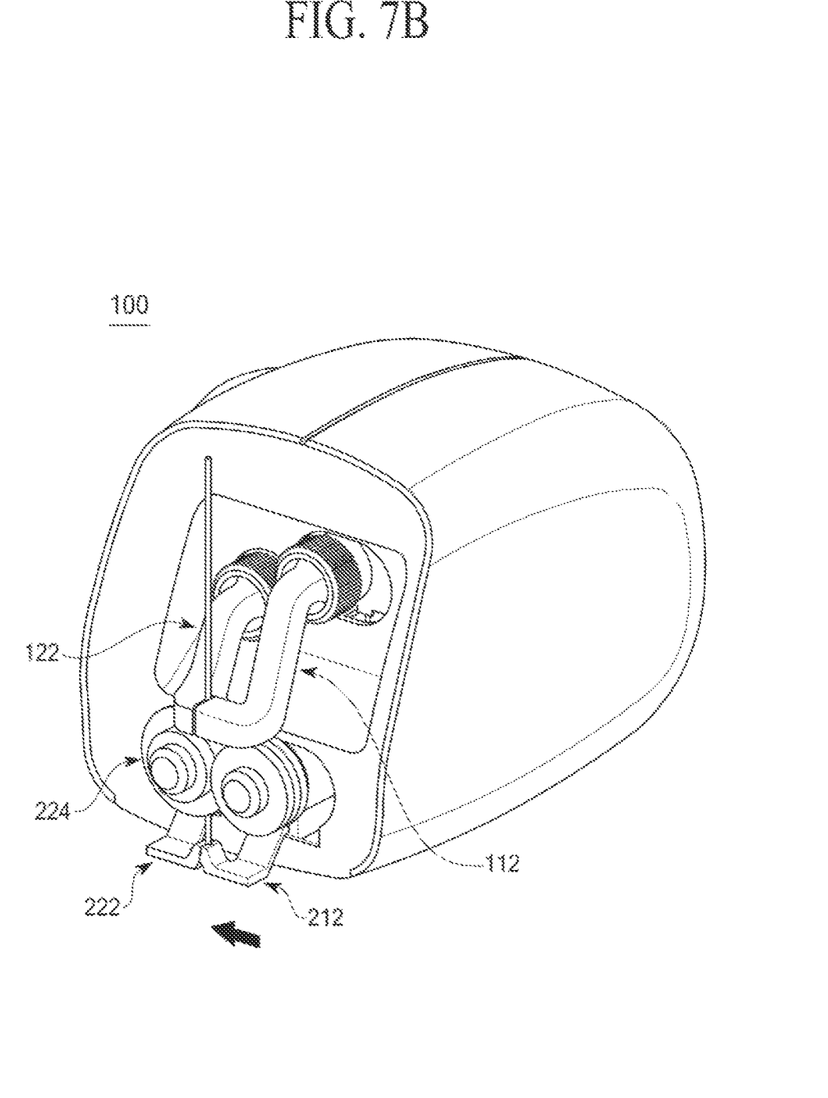

FIGS. 7A and 7B are exemplary diagrams for describing an operation of the medical intervention apparatus 100 according to an embodiment of the present invention.

Figure 4B:
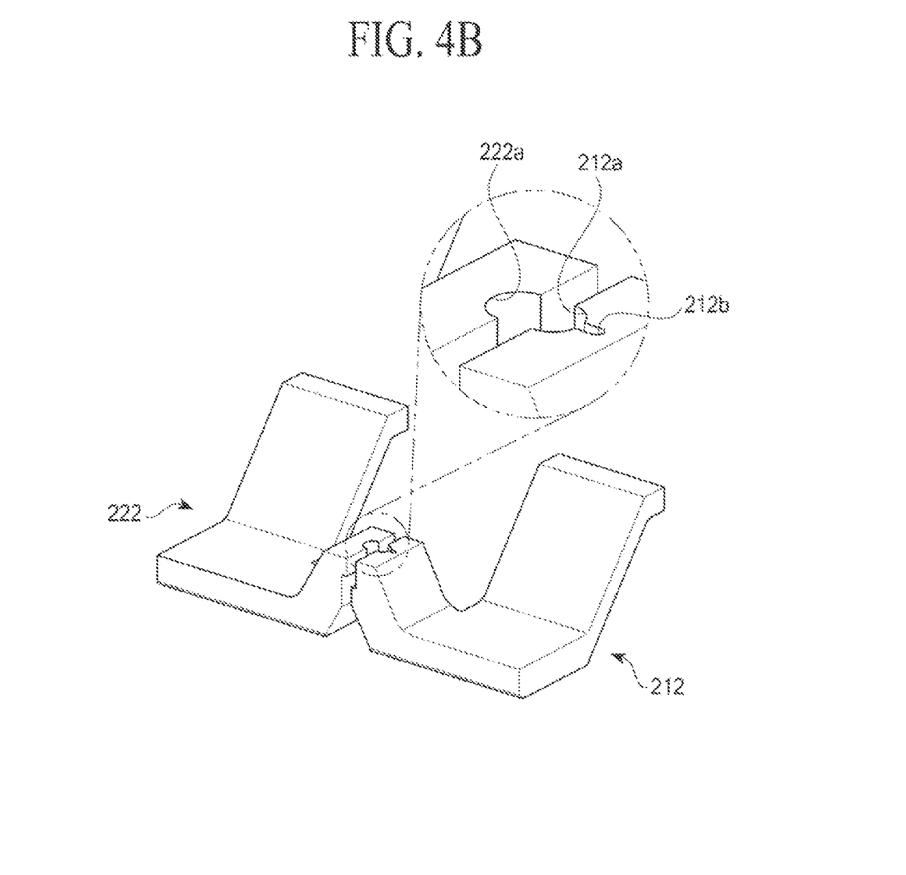
FIG. 4B is an exemplary diagram for describing first and second guide plates according to an embodiment of the present invention.

First, as illustrated in FIG. 7A, the first upper gripper 112 may be separated from the second upper gripper 122. Also, the first guide plate 212 and the first lower gripper 214 may be separated from the second guide plate 222 and the second lower gripper 224. The needle N may be accommodated in the accommodating groove (212b in FIG. 4B) of the first guide plate 212. After the needle N is accommodated, as illustrated in FIG. 7B, the first guide plate 212 and the first lower gripper 214 may rectilinearly move to the second guide plate 222 and the second lower gripper 224.

Subsequently, the first upper gripper 112 may rectilinearly move to the second upper gripper 122. As the first upper gripper 112 rectilinearly moves to the second upper gripper 122, the needle N accommodated in the accommodating groove (212b in FIG. 4B) of the first guide plate 212 may be pushed into the guide groove (212a in FIG. 4B) of the first guide plate 212.

By way of summation and review, by using the medical intervention apparatus 100 according to an embodiment of the present invention, medical staffs perform an interventional procedure at a position far away from a radiographic apparatus, and thus, the medical intervention apparatus 100 protects the medical staffs from radiation exposure and prevents the medical staffs from being damaged due to the radiation exposure. Also, an accuracy of an operation of inserting a needle into a human body for an interventional procedure is enhanced, and a time taken in inserting the needle into an accurate position is shortened. In addition, pain and agony which is applied to a patient in performing an interventional procedure are reduced.

In the medical intervention apparatus 100 according to an embodiment of the present invention, the first and second upper grippers, the first and second lower grippers, and the first and second guide plates are partially made of a radiolucent material, and thus, a radiolucency of near an insertion point is secured. Also, the medical intervention apparatus 100 according to an embodiment of the present invention includes the sterilization membrane, and thus, the sterilization membrane protects the medical intervention apparatus 100 from contamination which occurs in an interventional place.

In the medical intervention apparatus 100 according to an embodiment of the present invention, the first lower gripper includes the needle contact groove 2141 that is provided along a circumference to have a shape where a width is progressively narrowed in a direction from an outer circumference surface to a center portion, and the second lower gripper includes the protrusion that is inserted into the needle contact groove of the first lower gripper. Accordingly, three points of the needle are supported by the needle contact groove and the protrusion, and the medical intervention apparatus 100 can use a plurality of needles having different thicknesses.

In the medical intervention apparatus 100 according to an embodiment of the present invention, the first guide plate further includes the accommodating groove that accommodates the end of the needle and is connected to the first guide groove, and thus, a constant position of the needle supported by the first and second lower grippers is always maintained in preparing for an interventional procedure.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A medical intervention apparatus comprising:
   a needle rotation unit including a first needle rotation member, a second needle rotation member separate from the first needle rotation member, and a first driver that drives the first and second needle rotation members to move rectilinearly in opposite directions, wherein the first needle rotation member comprises:
      a first upper gripper coupling part configured to move backward and forward according to a driving force from the first driver, the first upper gripper coupling part having a first tap,
      a detachable first upper gripper attached to the first upper gripper coupling part, and
      a first fastening member fastened to the first tap and configured to support the first upper gripper, and
   the second needle rotation member comprises:
      a second upper gripper coupling part configured to move backward and forward according to the driving force from the first driver, the second upper gripper coupling part having a second tap,
      a detachable second upper gripper attached to the second upper gripper coupling part, and
      a second fastening member fastened to the second tap and configured to support the second upper gripper; and
   a needle insertion unit configured to insert a needle that is between the first needle rotation member and the second needle rotation member into a target.

2. The medical intervention apparatus of claim 1, wherein the needle insertion unit comprises:
   a first needle insertion member including (i) a first roller coupling part and a detachable first roller attached thereto, the first roller coupling part comprising a first roller bracket, (ii) a first guide plate in the first roller bracket that includes a first guide groove to guide the needle, and (iii) a detachable first lower gripper attached to the first roller;
   a second needle insertion member including (i) a second roller coupling part and a detachable second roller attached thereto, the second roller coupling part comprising a second roller bracket, (ii) a second guide plate in the second roller bracket that includes a second guide groove to guide the needle, and (iii) a detachable second lower gripper attached to the second roller; and
   a second driver configured to drive the first roller coupling part and rotate the first roller.

3. The medical intervention apparatus of claim 2, wherein:
   the first lower gripper comprises a needle contact groove along a circumference of the first lower gripper, and
   the second lower gripper comprises a protrusion in the needle contact groove.

4. The medical intervention apparatus of claim 3, wherein the first guide plate further comprises an accommodating groove connected to the first guide groove and configured to accommodate an end of the needle.

5. The medical intervention apparatus of claim 4, wherein:
the first driver is configured to drive the first needle rotation member closer to or farther away from the second needle rotation member, and
the second driver is configured to drive the first needle insertion member closer to or farther away from the second needle insertion member.

6. The medical intervention apparatus of claim 3, wherein:
the first driver is configured to drive the first needle rotation member closer to or farther away from the second needle rotation member, and
the second driver is configured to drive the first needle insertion member closer to or farther away from the second needle insertion member.

7. The medical intervention apparatus of claim 3, wherein the needle contact groove has a shape and/or a width that progressively narrows in a direction from an outer circumference surface to a center of the first lower gripper.

8. The medical intervention apparatus of claim 2, wherein the first guide plate further comprises an accommodating groove connected to the first guide groove and configured to accommodate an end of the needle.

9. The medical intervention apparatus of claim 8, wherein:
the first driver is configured to drive the first needle rotation member closer to or farther away from the second needle rotation member, and
the second driver is configured to drive the first needle insertion member closer to or farther away from the second needle insertion member.

10. The medical intervention apparatus of claim 2, wherein:
the first driver is configured to drive the first needle rotation member closer to or farther away from the second needle rotation member, and
the second driver is configured to drive the first needle insertion member closer to or farther away from the second needle insertion member.

11. The medical intervention apparatus of claim 2, further comprising a sterilization membrane,
wherein the sterilization membrane comprises:
a first fitting part into the first upper gripper coupling part;
a second fitting part into the second upper gripper coupling part;
a third fitting part into the first roller coupling part;
a fourth fitting part into the second roller coupling part;
a fifth fitting part, wherein the first guide plate is in the fifth fitting part; and
a sixth fitting part, wherein the second guide plate is in the sixth fitting part.

12. The medical intervention apparatus of claim 2, further comprising a sterilization membrane.

13. The medical intervention apparatus of claim 12, wherein the sterilization membrane comprises a first fitting part in the first upper gripper coupling part.

14. The medical intervention apparatus of claim 13, wherein the sterilization membrane further comprises a second fitting part in the second upper gripper coupling part.

15. The medical intervention apparatus of claim 14, wherein the sterilization membrane further comprises a third fitting part in the first roller coupling part.

16. The medical intervention apparatus of claim 15, wherein the sterilization membrane further comprises a fourth fitting part in the second roller coupling part.

17. The medical intervention apparatus of claim 16, wherein the sterilization membrane further comprises a fifth fitting part and a sixth fitting part, the first guide plate is in the fifth fitting part, and the second guide plate is in the sixth fitting part.

18. The medical intervention apparatus of claim 1, wherein the needle insertion unit comprises a first needle insertion member comprising:
a first roller coupling part comprising a first roller bracket,
a detachable first roller attached to the first roller coupling part,
a first guide plate in the first roller bracket that includes a first guide groove to guide the needle, and
a detachable first lower gripper attached to the first roller.

19. The medical intervention apparatus of claim 18, wherein the first needle insertion member further comprises a second driver configured to drive the first roller coupling part and rotate the first roller.

20. The medical intervention apparatus of claim 18, wherein the first needle insertion member further comprises a second needle insertion member comprising:
a second roller coupling part comprising a second roller bracket,
a detachable second roller attached to the second roller coupling part,
a second guide plate in the second roller bracket that includes a second guide groove to guide the needle, and
a detachable second lower gripper attached to the second roller.

* * * * *